US006369051B1

(12) United States Patent
Jenkins

(10) Patent No.: US 6,369,051 B1
(45) Date of Patent: Apr. 9, 2002

(54) COMBINATIONS OF SSRI AND ESTROGENIC AGENTS

(75) Inventor: Simon Nicholas Jenkins, Audubon, PA (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/896,361

(22) Filed: Jun. 29, 2001

Related U.S. Application Data

(60) Provisional application No. 60/216,408, filed on Jul. 6, 2000.

(51) Int. Cl.$^7$ ............... A61K 31/55; A61K 31/395; A61K 31/53; A61K 31/445; A61K 31/40; A61K 31/15; A61K 31/135
(52) U.S. Cl. ............... 514/217.08; 514/210.21; 514/244; 514/321; 514/323; 514/414; 514/640; 514/649; 514/653; 514/657
(58) Field of Search ............... 514/217.08, 323, 514/210.21, 414, 244, 649, 321, 657, 640, 653

(56) References Cited

U.S. PATENT DOCUMENTS 5,780,497 A    7/1998   Miller et al.
5,880,137 A    3/1999   Miller et al.

FOREIGN PATENT DOCUMENTS

EP     0802184 A1   10/1997
WO     WO99/19293    4/1999

Primary Examiner—William R. A. Jarvis
(74) Attorney, Agent, or Firm—Arnold S. Milowsky

(57) ABSTRACT

This invention comprises methods of depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome comprising administration of a selective serotonin reuptake inhibitor and compound of the formulae I or II:

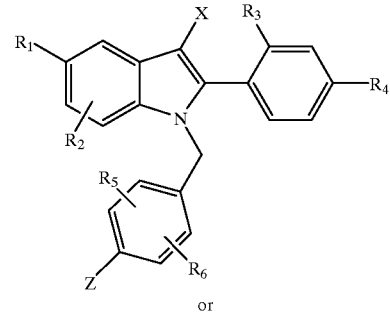

or

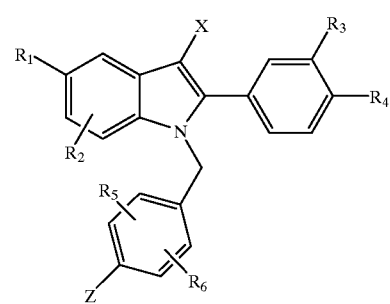

wherein Z is a moiety selected from the group of:

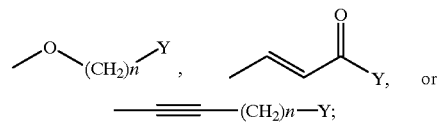

wherein:

$R_1$ is selected from H, OH or the $C_1$–$C_{12}$ esters or $C_1$–$C_{12}$ alkyl ethers thereof, benzyloxy, or halogen; or $C_1$–$C_4$ halogenated ethers including trifluoromethyl ether and trichloromethyl ether; $R_2$, $R_3$, $R_4$, $R_5$, and $R_6$ are H, OH or $C_1$–$C_{12}$ esters or $C_1$–$C_{12}$ alkyl ethers thereof, halogens, or $C_1$–$C_4$ halogenated ethers, cyano, $C_1$–$C_6$ alkyl, or trifluoromethyl, with the proviso that, when $R_1$ is H, $R_2$ is not OH; Y is the moiety:

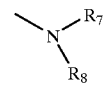

$R_7$ and $R_8$ are alkyl or concatenated together to form an optionally substituted, nitrogen-containing ring; or a pharmaceutically acceptable salt thereof.

16 Claims, No Drawings

COMBINATIONS OF SSRI AND ESTROGENIC AGENTS

This application claims the benefit of U.S. Provisional Application No. 60/216,408, filed Jul. 6, 2000.

This invention relates to methods of using substituted indole compounds in the combination with a selective serotonin reuptake inhibitor (SSRI) for the treatment, prevention, inhibition or alleviation of depression, anxiety, generalized anxiety disorder (GAD), hot flush, post partum depression, premenstrual syndrome, obesity, obsessive compulsive disorder, social phobia, disruptive behavior disorders, impulse control disorders, borderline personality disorder, chronic fatigue disorder, premature ejaculation, pain, post-traumatic stress disorder, attention deficit disorders, with and without hyperactivity, Gilles de la Tourette syndrome, bulimia nervosa, or Shy Drager Syndrome and related pharmaceutical compositions and kits.

BACKGROUND OF THE INVENTION

EP 0 802 183 A1 and U.S. Pat. No. 5,780,497 describe substituted indole compounds of the formulae below:

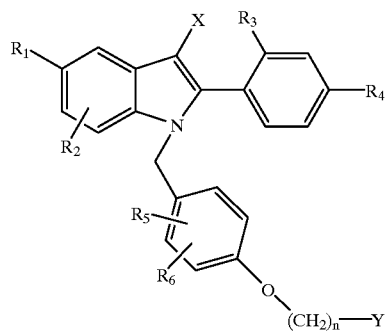

or

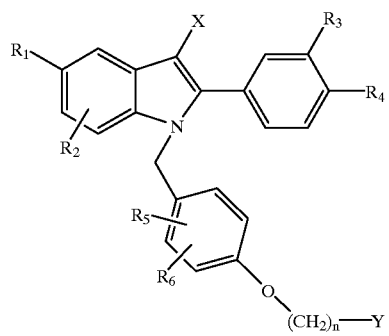

as well as their use as estrogenic agents, including the treatment of bone loss, cardiovascular disease, maladies associated with or resulting from the proliferation or abnormal development of endometrial or endometrial-like tissues, and disease states or syndromes associated with estrogen deficiency.

EP 0 802 184 A1, published Oct. 22, 1997, describes comparable uses for substituted indole compounds of the formulae below.

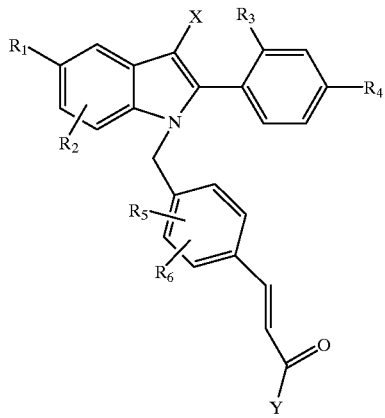

or

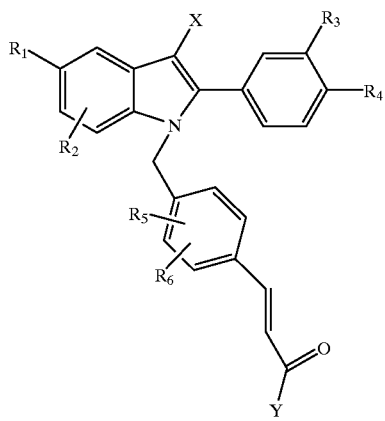

Analogous indole compounds having the general structures:

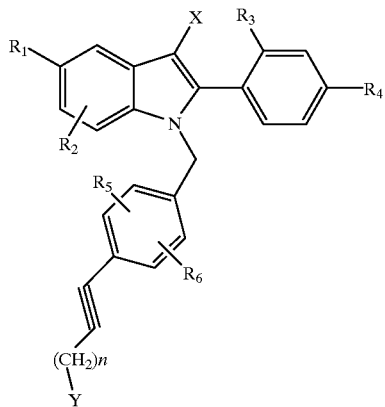

or

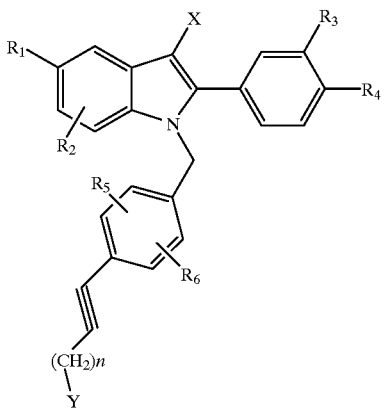

are described in U.S. Pat. No. 5,880,137 (Miller et al.).

Filipponi P et al: Cyclical clodronate is effective in preventing postmenopausal bone loss: A comparative study with transcutaneous hormone replacement therapy. J Bone Min Res 10:697–703, 1995.

DESCRIPTION OF THE INVENTION

This invention comprises methods of treating, preventing, alleviating or inhibiting depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome in a mammal, preferably in a human, the methods comprising administering to a mammal in need thereof a pharmaceutically effective combination of:

a) a pharmaceutically effective amount of a selective serotonin reuptake inhibitor (SSRI), or a pharmaceutically effective salt thereof; and b) a pharmaceutically effective amount of a substituted indole compound of the formulae I or II, below:

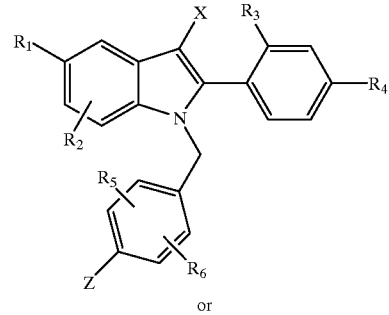

or

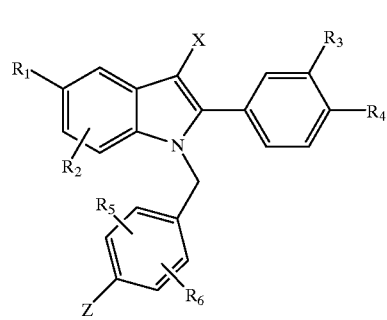

wherein Z is a moiety selected from the group of:

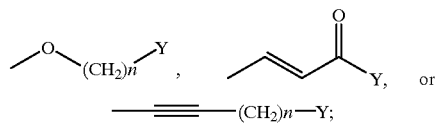

wherein:

$R_1$ is selected from H, OH or the $C_1$–$C_{12}$ esters (straight chain or branched) or $C_1$–$C_{12}$ (straight chain or branched or cyclic) alkyl ethers thereof, benzyloxy, or halogens; or $C_1$–$C_4$ halogenated ethers including trifluoromethyl ether and trichloromethyl ether.

$R_2$, $R_3$, $R_5$, and $R_6$ are independently selected from H, OH or the $C_1$–$C_{12}$ esters (straight chain or branched) or $C_1$–$C_{12}$ alkyl ethers (straight chain or branched or cyclic) thereof, halogens, or $C_1$–$C_4$ halogenated ethers including trifluoromethyl ether and trichloromethyl ether, cyano, $C_1$–$C_6$ alkyl (straight chain or branched), or trifluoromethyl, with the proviso that, when $R_1$ is H, $R_2$ is not OH;

$R_4$ is selected from H, OH or the $C_1$–$C_{12}$ esters (straight chain or branched) or $C_1$–$C_{12}$ alkyl ethers (straight chain or branched or cyclic) thereof, benzyloxy, halogens, or $C_1$–$C_4$ halogenated ethers including trifluoromethyl ether and trichloromethyl ether, cyano, $C_1$–$C_6$ alkyl (straight chain or branched), or trifluoromethyl;

X is selected from H, $C_1$–$C_6$ alkyl, cyano, nitro, trifluoromethyl, halogen;

n is 1, 2 or 3;

Y is selected from:

a) the moiety:

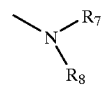

wherein $R_7$ and $R_8$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy $(C_1$–$C_4)$alkyl, —$CO_2H$—, —CN—, —$CONHR_1$—, —$NH_2$—, $C_1$–$C_4$ alkylamino, di($C_1$–$C_4$)alkylamino, —$NHSO_2R_1$—, —$NHCOR_1$—, —$NO_2$, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy $(C_1$–$C_4)$alkyl, —$CO_2H$—, —CN—, —$COHNR_1$—, —$NH_2$—, $C_1$–$C_4$ alkylamino, di($C_1$–$C_4$)alkylamino, —$NHSO_2R_1$—, —$NHCOR_1$—, —$NO_2$, and phenyl optionally substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1C_4$ alkyl)-, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy $(C_1$–$C_4)$alkyl, —$CO_2H$—, —CN—, —$CONHR_1$—, —$NH_2$—, $C_1$–$C_4$ alkylamino, di($C_1$–$C_4$)alkylamino, —$NHSO_2R_1$—, —$NHCOR_1$—, —$NO_2$, and phenyl optionally substituted with 1–3 ($C_1$–$C_4$)alkyl; or e) a bicyclic heterocycle containing from 6–12 carbon atoms either bridged or fused and containing up to two heteroatoms selected from the group consisting of —O—, —NH—, —N($C_1C_4$ alkyl)-, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy $(C_1$–$C_4)$alkyl, —$CO_2H$—, —CN—, —$CONHR_1$—, —$NH_2$—, $C_1$–$C_4$ alkylamino, di($C_1$–$C_4$)alkylamino, —$NHSO_2R_1$—, —$NHCOR_1$—, —$NO_2$, and phenyl optionally substituted with 1–3 ($C_1$–$C_4$) alkyl;

and the pharmaceutically acceptable salts thereof.

The more preferred substituted indole compounds of this invention are those having the general structures I or II, above, wherein:

$R_1$ is selected from H, OH or the $C_1$–$C_{12}$ esters or alkyl ethers thereof, benzyloxy, or halogen;

$R_2$, $R_3$, $R_5$, and $R_6$ are independently selected from H, OH or the $C_1$–$C_{12}$ esters or alkyl ethers thereof, halogen, cyano, $C_1$–$C_6$ alkyl, or trihalomethyl, preferably trifluoromethyl, with the proviso that, when $R_1$ is H, $R_2$ is not OH;

$R_4$ is selected from H, OH or the $C_1$–$C_{12}$ esters or alkyl ethers thereof, benzyloxy, halogen, cyano, $C_1$–$C_6$ alkyl, or trihalomethyl;

X is selected from H, $C_1$–$C_6$ alkyl, cyano, nitro, trifluoromethyl, halogen;

Y is the moiety

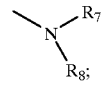

$R_7$ and $R_8$ are selected independently from H, $C_1$–$C_6$ alkyl, or combined by —$(CH_2)_p$—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy $(C_1$–$C_4)$alkyl, —$CO_2H$, —CN, —CONH($C_1$–$C_4$), —$NH_3$, $C_1$–$C_4$ alkylamino, $C_1$–$C_4$ dialkylamino, —$NHSO_2(C_1$–$C_4)$, —NHCO $(C_1$–$C_4)$, and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred substituted indole compounds of the present invention are those having the structural formulas I or II, above, wherein $R_1$ is OH; $R_2$–$R_6$ are as defined above; X is selected from the group of Cl, $NO_2$, CN, $CF_3$, or $CH_3$; and Y is the moiety

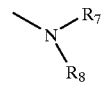

and $R_7$ and $R_8$ are concatenated together as —$(CH_2)_r$—, wherein r is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$) alkyl, —$NH_2$, $C_1$–$C_4$ alkylamino, di($C_1$–$C_4$)alkylamino, —$NHSO_2(C_1$–$C_4)$alkyl, —NHCO($C_1$–$C_4$)alkyl, and —$NO_2$;

and the pharmaceutically acceptable salts thereof.

In another embodiment of this invention, when $R_7$ and $R_8$ are concatenated together as —$(CH_2)_p$—, wherein p is an integer of from 2 to 6, preferably 4 to 6, the ring so formed is optionally substituted with 1–3 substituents selected from a group containing $C_1$–$C_3$ alkyl, trifluoromethyl, halogen, hydrogen, phenyl, nitro, —CN.

The invention includes sulfate, sulfamates and sulfate esters of phenolic groups of the substituted indoles. Sulfates can be readily prepared by the reaction of the free phenolic compounds with sulfur trioxide complexed with an amine such as pyridine, trimethylamine, triethylamine, etc. Sulfamates can be prepared by treating the free phenolic compound with the desired amino or alkylamino or dialkylamino sulfamyl chloride in the presence of a suitable base such as pyridine. Sulfate esters can be prepared by reaction of the free phenol with the desired alkanesulfonyl chloride in the presence of a suitable base such as pyridine. Additionally, this invention includes compounds containing phosphates at the phenol as well as dialkyl phosphates. Phosphates can be prepared by reaction of the phenol with the appropriate chlorophosphate. The dialkylphosphates can be hydrolyzed to yield the free phosphates. Phosphinates are also claimed where the phenol is reacted with the desired dialkylphosphinic chloride to yield the desired dialkylphosphinate of the phenol.

The invention includes acceptable salt forms of the substituted indole formed from the addition reaction with either inorganic or organic acids. Inorganic acids such as hydrochloric acid, hydrobromic acid, hydroiodic acid, sulfuric acid, phosphoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and nonprotic) and usually it is preferred to administer a compound of this invention in the form of an acid addition salt. Additionally, this invention includes quaternary ammonium salts of the compounds herein. These can be prepared by reacting the nucleophilic amines of the side chain with a suitably reactive alkylating agent such as an alkyl halide or benzyl halide.

The present invention includes methods for treating pain using the combinations described herein. Pain in these instances includes, but is not limited to, neuropathic pain, chronic pain, musculoskeletal pain, cancer pains, fibromyalgia, psychogenic pain, neurogenic pain, facial neuralgias and pain associated with shingles.

These methods each comprise administering to a mammal in need thereof a pharmaceutically effective amount of a SSRI agent and a pharmaceutically effective amount of one of the substituted indoles taught herein, or a pharmaceutically acceptable salt of either of these agents. These administrations may be therapeutic or prophylactic. Among the preferred substituted indole compounds for use in these methods are 1-[4-(2-Azepan-1-yl-ethoxy)-benzyl]-2-(4-hydroxy-phenyl)-3-methyl-1H-indol-5-ol, also known as TSE-424,and 2-(4-Hydroxy-phenyl)-3-methyl-1-[4-(2-piperidin-1-yl-ethoxy)-benzyl]-1H-indol-5-ol, also known as ERA-923.

SSRI agents useful with the present methods of treatment include, but are not limited to, venlafaxine, fluoxetine, paroxetine, sertraline, or fluvoxamine, or a pharmaceutically acceptable salt thereof.

The present invention includes methods utilizing in conjunction with a SSRI compound a first subset or subgroup of substituted indole compounds of the formulas IIII or IV, below:

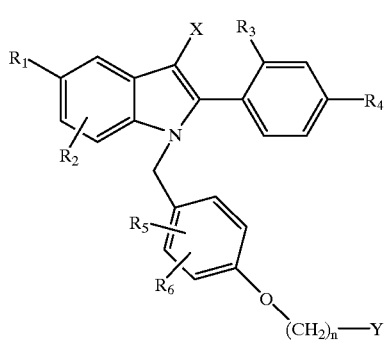

(II)

-continued
or

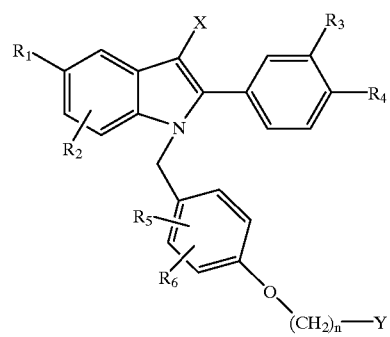

(IV)

wherein the variable substituents including $R_1$, $R_2$, $R_3$, $R_4$, $R_5$, $R_6$, n, X, and Y are as defined above, or a pharmaceutically acceptable salt thereof.

The more preferred substituted indole compounds of this first subset of compounds are those having the general structures IIII or IV, above, wherein:

$R_1$ is selected from H, OH or the $C_1$–$C_{12}$ esters or alkyl ethers thereof, benzyloxy, or halogen;

$R_2$, $R_3$, $R_5$, and $R_6$ are independently selected from H, OH or the $C_1$–$C_{12}$ esters or alkyl ethers thereof, halogen, cyano, $C_1$–$C_6$ alkyl, or trihalomethyl, preferably trifluoromethyl, with the proviso that, when $R_1$ is H, $R_2$ is not OH;

$R_4$ is selected from H, OH or the $C_1$–$C_{12}$ esters or alkyl ethers thereof, benzyloxy, halogen, cyano, $C_1$–$C_6$ alkyl, or trihalomethyl;

X is selected from H, $C_1$–$C_6$ alkyl, cyano, nitro, trifluoromethyl, halogen;

Y is the moiety

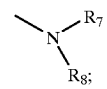

$R_7$ and $R_8$ are selected independently from H, $C_1$–$C_6$ alkyl, or combined by —$(CH_2)_p$—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_3$, $C_1$–$C_4$ alkylamino, $C_1$–$C_4$ dialkylamino, —$NHSO_2$($C_1$–$C_4$), —NHCO ($C_1$–$C_4$), and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred substituted indole compounds of this first subset of compounds are those having the structural formulas I or II, above, wherein $R_1$ is OH; $R_2$–$R_6$ are as defined above; X is selected from the group of Cl, $NO_2$, CN, $CF_3$, or $CH_3$; and Y is the moiety

and R$_7$ and R$_8$ are concatenated together as —(CH$_2$)$_r$—, wherein r is an integer of from 4 to 6, to form a ring optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$) alkyl, —NH$_2$, C$_1$–C$_4$ alkylamino, di(C$_1$–C$_4$)alkylamino, —NHSO$_2$(C$_1$–C$_4$)alkyl, —NHCO(C$_1$–C$_4$)alkyl, and —NO$_2$;

and the pharmaceutically acceptable salts thereof.

In another embodiment of this first subset of compounds, when R$_7$ and R$_8$ are concatenated together as —(CH$_2$)$_p$—, wherein p is an integer of from 2 to 6, preferably 4 to 6, the ring so formed is optionally substituted with 1–3 substituents selected from a group containing C$_1$–C$_3$ alkyl, trifluoromethyl, halogen, hydrogen, phenyl, nitro, —CN.

Among the preferred compounds of this first subset of substituted indoles are the following:

5-Benzyloxy-2-(4-ethoxy-phenyl)-3-methyl-1-[4-(2-piperidin-1-yl-ethoxy)-benzyl]-1H-indole;
5-Benzyloxy-2-phenyl-3-methyl-1-[4-(2-azepan-1-yl-ethoxy)-benzyl]-1H-indole;
5-Benzyloxy-2-(4-benzyloxy-phenyl)-3-methyl-1-[4-(2-azepan-1-yl-ethoxy)-benzyl]-1-indole;
5-Benzyloxy-2-(4-benzyloxy-phenyl)-3-methyl-1-[4-(2-diisopropylamino-1-yl-ethoxy)-benzyl]-1H-indole;
5-Benzyloxy-2-(4-benzyloxy-phenyl)-3-methyl-1-[4-(2-butyl-methylamino-1-ylethoxy)-benzyl]-1H-indole;
5-Benzyloxy-2-(4-benzyloxy-phenyl)-3-methyl-1-{4-dimethylamino)-ethoxy]-benzyl}-1H-indole;
5-Benzyloxy-2-(4-benzyloxy-phenyl)-3-methyl-1-{4-[2-(2-methyl-piperidin-1-yl)-ethoxy]benzyl}-1H-indole;
5-Benzyloxy-2-(4-benzyloxy-phenyl)-3-methyl-1-{4-[2-(3-methyl-piperidin-1-yl)-ethoxy]-benzyl}-1H-indole;
5-Benzyloxy-2-(4-benzyloxy-phenyl)-3-methyl-1-{4-[2-(4-methyl-piperidin-1-yl)-ethoxy]-benzyl}-1H-indole;
5-Benzyloxy-2-(4-benzyloxy-phenyl)-3-methyl-1{4-[2-((cis)-2,6-Dimethyl-piperidin-1-yl)-ethoxy]-benzyl}-1H-indole;
5-Benzyloxy-2-(4-benzyloxy-phenyl)-3-methyl-{4-[2-(1,3,3-trimethyl-6-aza-bicyclo[3.2.1]oct-6-yl)-ethoxy]-benzyl}-1H-indole;
(1S,4R)-5-Benzyloxy-2-(4-benzyloxy-phenyl)-3-methyl{4-[2-(2-Aza-bicyclo[2.2.1]hept-2-yl)-ethoxy]-benzyl}-1H-indole;
5-Benzyloxy-2-(4-flouro-phenyl)-3-methyl-1-[4-(2-azepan-1-yl-ethoxy)-benzyl]-1H-indole;
5-Benzyloxy-2-(4-flouro-phenyl)-3-methyl-1-[4-(2-piperidin-1-yl-ethoxy)-benzyl]-1H-indole;
5-Benzyloxy-2-(4-chloro-phenyl)-3-methyl-1-[4-(2-piperidin-1-yl-ethoxy)-benzyl]-1H-indole;
5-Benzyloxy-2-[3,4-methylenedioxy-phenyl]-3-methyl-1-[4-(2-piperidin-1-yl-ethoxy)-benzyl]-1H-indole;
5-Benzyloxy-2-[4-isopropoxy-phenyl]-3-methyl-1-[4-(2-piperidin-1-yl-ethoxy)-benzyl]-1H-indole;
5-Benzyloxy-2-[4-methyl-phenyl]-3-methyl-1-[4-(2-piperidin-1-yl-ethoxy)-benzyl]-1H-indole;
1-[4-(2-Azepan-1-yl-ethoxy)-benzyl]-5-benzyloxy-2-(3-benzyloxy-phenyl)-3-methyl-1H-indole;
5-Benzyloxy-2-(4-benzyloxy-3-fluoro-phenyl)-3-methyl-1-[4-(2-piperidin-1-yl-ethoxy)-benzyl]-1H-indole;
5-Benzyloxy-2-(4-benzyloxy-3-fluoro-phenyl)-3-methyl-1-[4-(2-azepan-1-yl-ethoxy)-benzyl]-1H-indole;
5-Benzyloxy-2-(3-methoxy-phenyl-1-[4-(2-piperidin-1-yl-ethoxy)-benzyl]-3-methyl-1H-indole;
5-Benzyloxy-3-methyl-1-[4-(2-piperidin-1-yl-ethoxy)-benzyl]-2-(4-trifluoromethoxy-phenyl)-1H-indole;
(2-{4-[5-Benzyloxy-2-(4-benzyloxy-phenyl)-3-methyl-indol-1-ylmethyl]-phenoxy}-ethyl)-cyclohexyl-amine;
5-Benzyloxy-2-(4-benzyloxy-phenyl)-3-methyl-1-{4-methylpiperazin-1-yl)-ethoxy]-benzyl}-1H-indole;
1-[4-(2-Azepan-1-yl-ethoxy)-benzyl]-5-benzyloxy-2-(3-methoxy-phenyl)-3-methyl-1H-indole;
4-{3-Methyl-1-[4-(2-piperidin-1-yl-ethoxy)-benzyl]-1H-indole};
4-{3-Methyl-1-[4-(2-piperidin-1-yl-ethoxy)-benzyl]-1H-indol-2-yl}-phenol;
3-Methyl-2-phenyl-1-[4-(2-piperidine-1-yl-ethoxy)-benzyl]-1H-indol-5-ol;
4-{5-Methoxy-3-methyl-1-{4-[2-(piperidin-1-yl)-ethoxy]-benzyl}-1H-indol-2-yl}-phenol;
2-(4-methoxy-phenyl)-3-methyl-1-{4-[2-(piperidin-1-yl)-ethoxy]-benzyl}-1H-indol-5-ol;
5-Methoxy-2-(4-methoxy-phenyl)-3-methyl-1-[4-(2-piperidin-1-yl-ethoxy)-benzyl]-1H-indole;
1-[4-(2-Azepan-1-yl-ethoxy)-benzyl]-5-methoxy-2-(4-methoxy-phenyl)-3-methyl-1H-indole;
2-(4-Ethoxy-phenyl)-3-methyl-1-[4-(2-piperidin-1-yl-ethoxy)-benzyl]-1H-indol-5-ol;
1-[4-(2-Azepan-1-yl-ethoxy)-benzyl]-2-(4-ethoxy-phenyl)-3-methyl-1H-indol-5-ol;
4-{5-Fluoro-3-methyl-1-[4-(2-piperidin-1-yl-ethoxy)-benzyl]-1H-indol-2-yl}-phenol;
1-[4-(2-Azepan-1-yl-ethoxy)-benzyl]-3-methyl-2-phenyl-1H-indol-5-ol;
2-(4-Hydroxy-phenyl)-3-methyl-1-[4-(2-pyrollidin-1-yl-ethoxy)-benzyl]-1H-indol-5-ol;
1-[4-(2-Azepan-1-yl-ethoxy)-benzyl]-2-(4-hydroxy-phenyl)-3-methyl-1H-indol-5-ol;
1-[4-(2-Azocan-1-yl-ethoxy)-benzyl]-2-(4-hydroxy-phenyl)-3-methyl-1H-indol-5-ol;
2-(4-Hydroxy-phenyl)-3-methyl-1-[4-(2-dimethyl-1-yl-ethoxy)-benzyl]-1H-indol-5-ol;
2-(4-Hydroxy-phenyl)-3-methyl-1-[4-(2-diethyl-1-yl-ethoxy)-benzyl]-1H-indol-5-ol;
1-[4-(2-Dipropylamino-ethoxy)-benzyl]-2-(4-hydroxy-phenyl)-3-methyl-1H-indol-5-ol;
1-[4-(2-Dibutylamino-ethoxy)-benzyl]-2-(4-hydroxy-phenyl)-3-methyl-1H-indol-5-ol;
1-[4-(2-Diisopropylamino-ethoxy)-benzyl]-2-(4-hydroxy-phenyl)-3-methyl-1H-indol-5-ol;
1-{4-[2-(Butyl-methyl-amino)-ethoxy]-benzyl}-2-(4-hydroxy-phenyl)-3-methyl-1H-indol-5-ol;
2-(4-Hydroxy-phenyl)-3-methyl-1-{4-[2-(2-methyl-piperidin-1-yl)-ethoxy]-benzyl}-1H-indol-5-ol;
2-(4-Hydroxy-phenyl)-3-methyl-1-{4-[2-(3-methyl-piperdin-1-yl)-ethoxy]-benzyl}-1H-indol-5-ol;
2-(4-Hydroxy-phenyl)-3-methyl-1-{4-[2-(4-methyl-piperidin-1-yl)-ethoxy]-benzyl}-1H-indol-5-ol;
1-{4-[2-(3,3-Dimethyl-piperidin-1-yl)-ethoxy]-benzyl}-2-(4-hydroxy-phenyl)-3-methyl-1H-indol-5-ol;
1-{4-[2-((cis)-2,6-Dimethyl-piperidin-1-yl)-ethoxy]-benzyl}-2-(4-hydroxy-phenyl)-3-methyl-1H-indol-5-ol;
2-(4-Hydroxy-phenyl)-1-{4-[2-(4-hydroxy-piperidin-1-yl)-ethoxy]-benzyl}-3-methyl-1H-indol-5-ol;
(1S,4R)-1-{4-[2-(2-Aza-bicyclo [2.2.1] hept-2-yl)-ethoxy]-benzyl}-2-(4-hydroxy-phenyl)-3-methyl-1H-indol-5-ol;
2-(4-Hydroxy-phenyl)-3-methyl-1-{4-[2-(1,3,3-trimethyl-6-aza-bicyclo[3.2.1]oct-6-yl)-ethoxy]-benzyl}-1H-indol-5-ol;

2-(4-Fluoro-phenyl)-3-methyl-1-[4-(2-piperidine-1-yl-ethoxy)-benzyl]-1H-indol-5-ol;
1-[4-(2-Azepan-1-yl-ethoxy)-benzyl]-2-(4-fluoro-phenyl)-3-methyl-1H-indol-5-ol;
2-(3-Methoxy-4-hydroxy-phenyl)-3-methyl-1-[4-(2-piperidin-1-yl-ethoxy)-benzyl]-1H-indol-5-ol;
2-Benzo[1,3]dioxol-5-yl-3-methyl-1-[4-(2-piperidin-1-yl-ethoxy)-benzyl]-1H-indol-5-ol;
2-(4-Isopropoxy-phenyl)-3-methyl-1-[4-(2-piperidin-1-yl-ethoxy)-benzyl]-1H-indol-5-ol;
1-[4-(2-Azepan-1-yl-ethoxy)-benzyl]-2-(4-isopropoxy-phenyl)-3-methyl-1H-indol-5-ol;
2-(4-Cyclopenyloxy-phenyl)-3-methyl-1-[4-(2-piperidin-1-yl-ethoxy)-benzyl]-1H-indol-5-ol;
3-Methyl-1-[4-(2-piperidin-1-yl-ethoxy)-benzyl]-2-(4-trifluoromethyl-phenyl)-1H-indol-5-ol;
3-Methyl-1-[4-(2-piperidin-1-yl-ethoxy)-benzyl]-2-p-tolyl-1H-indol-5-ol;
2-(4-Chloro-phenyl)-3-methyl-1-[4-(2-piperidin-1-yl-ethoxy)-benzyl]-1H-indol-5-ol;
2-(2,4-Dimethoxy-phenyl)-3-methyl-1-[4-(2-piperidin-1-yl-ethoxy)-benzyl]-1H-indol-5-ol;
2-(3-Hydroxy-phenyl)-3-methyl-1-[4-(2-piperidin-1-yl-ethoxy)-benzyl]-1H-indol-5-ol;
1-[4-(2-Azepan-1-yl-ethoxy)-benzyl]-2-(3-hydroxy-phenyl)-3-methyl-1H-indole-5-ol;
2-(3-Fluoro-4-hydroxy-phenyl)-3-methyl-1-[4-(2-piperidin-1-yl-ethoxy)-benzyl]-1H-indol-5-ol;
2-(3-Fluoro-4-hydroxy-phenyl)-3-methyl-1-[4-(azepan-1-yl-ethoxy)-benzyl]-1H-indol-5-ol;
2-(3-Methoxy-phenyl)-3-methyl-1-[4-(2-piperidin-1-yl-ethoxy)-benzyl]-1H-indole-5-ol;
3-Methyl-1-[4-(2-piperidin-1-yl-ethoxy)-benzyl]-2-(4-trifluoromethoxy-phenyl)-1H-indol-5-ol;
3-Chloro-2-(4-hydroxy-phenyl)-1-[4-(2-pyrrolidin-1-yl-ethoxy)-benzyl]-1H-indol-5-ol;
3-Chloro-2-(4-hydroxy-phenyl)-1-[4-(2-piperidin-1-yl-ethoxy)-benzyl]-1H-indol-5-ol;
3-Chloro-2-(4-hydroxy-phenyl)-1-[4-(2-azepan-1-yl-ethoxy)-benzyl]-1H-indol-5-ol;
3-Chloro-2-(4-hydroxy-2-methyl-phenyl)-1-[4-(2-piperidin-1-yl-ethoxy)-benzyl]-1H-indol-5-ol;
2-(4-Hydroxy-phenyl)-3-ethyl-1-[4-(2-piperidin-1-yl-ethoxy)-benzyl]-1H-indol-5-ol;
5-Hydroxy-2-(4-Hydroxy-phenyl)-1-[4-(2-piperidin-1-yl-ethoxy)-benzyl]-1H-indole-3-carbonitrile;
1-[4-(2-Azepan-1-yl-ethoxy)-benzyl]-5-hydroxy-2-(4-hydroxy-phenyl)-1H-indole-3-cabonitrile;
5-Benzyloxy-2-(4-benzyloxy-phenyl)-3-chloro-1-[4-(2-piperidin-1-yl-ethoxy)-benzyl]-1H-indole;
5-Benzyloxy-2-(4-benzyloxy-phenyl)-3-chloro-1-[4-(2-azepan-1-yl-ethoxy)-benzyl]-1H-indole;
5-Benzyloxy-2-(2-methyl-4-benzyloxy-phenyl)-3-chloro-1-[4-(2-piperidin-1-yl-ethoxy)-benzyl]-1H-indole;
5-Benzyloxy-2-(4-benzyloxy-phenyl)-3-ethyl-1-[4-(2-piperidin-1-yl-ethoxy)-benzyl]-1H-indole;
5-Benzyloxy-2-(4-benzyloxy-phenyl)-3-cyano-1-[4-(2-piperidin-1-yl-ethoxy)-benzyl]-1H-indole;
5-Benzyloxy-2-(4-benzyloxy-phenyl)-3-cyano-1-[4-(2-azepan-1-yl-ethoxy)-benzyl]-1H-indole;
Di-propionate of 1-[4-(2-Azepan-1-yl-ethoxy)-benzyl]-2-(4-hydroxy-phenyl)-3-methyl-1H-indol-5-ol;
Di-pivalate of 1-[4-(2-Azepan-1-yl-ethoxy)-benzyl]-2-(4-hydroxy-phenyl)-3-methyl-1H-indol-5-ol;
5-Benzyloxy-2-(4-benzyloxy-phenyl)-1-[4-(3-piperidin-1-yl-propoxy)-benzyl]-3-methyl-1H-indole;
2-(4-Hydroxy-phenyl)-3-methyl-1-{4-[3-(piperidin-1-yl)-propoxy]-benzyl}-1H-indol-5-ol;
2-(4-Hydroxy-phenyl)-1-[3-methoxy-4-(2-piperidin-1-yl-ethoxy)-benzyl]-3-methyl-1H-indol-5-ol;
2-(4-Hydroxy-phenyl)-1-[3-methoxy-4-(2-azepan-1-yl-ethoxy)-benzyl]-3-methyl-1H-indol-5-ol;
5-Benzyloxy-2-(4-benzyloxy-phenyl)-3-methyl-1-[3-Methoxy-4-(2-piperidin-1-yl-ethoxy)-benzyl]-1H-indole;
5-Benzyloxy-2-(4-benzyloxy-phenyl)-3-methyl-1-[2-Methoxy-4-(2-azepan-1-yl-ethoxy)-benzyl]-1H-indole;
2-(4-Hydroxy-phenyl)-3-methyl-1-[4-(2-piperidin-1-yl-ethoxy)-benzyl]-1H-indol-5-ol; or the pharmaceutically acceptable salts thereof.

The compounds of this first subset or subgroup of compounds can be produced by the methods described in EP 0 802 183A1, published Oct. 22, 1997, and U.S. Pat. No. 5,780,497, the subject matter of which is incorporated herein by reference, or by other methods known in the art. Aryloxy-alkyl-dialkylamines or aryloxy-alkyl-cyclic amines useful as intermediates in the production of the compounds above can be produced and used as disclosed in WO 99/19293, published Apr. 22, 1999, the subject matter of which is also incorporated herein by reference.

A second subset or subgroup of substituted indole compounds useful with this invention includes those of formulas (V) or (VI), below:

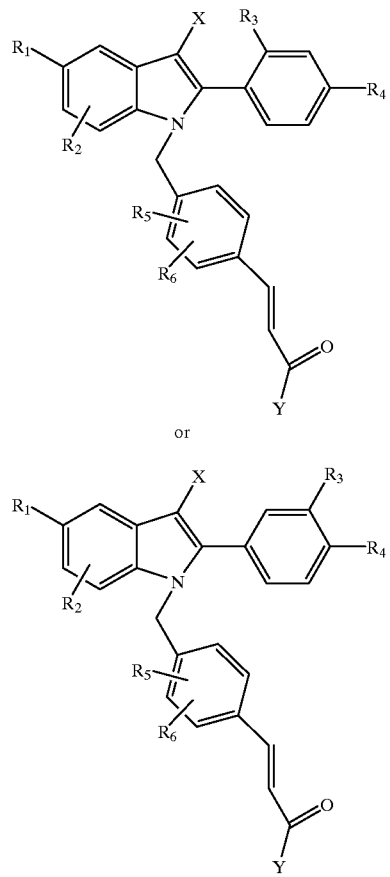

wherein the variable substituents including $R_1$, $R_2$, $R_3$, $R_4$, $R_5$, $R_6$, n, X, and Y are as defined above, or a pharmaceutically acceptable salt thereof.

Among the preferred substituted indole compounds of this second subset or subgroup are the following:

(E)-N,N-Diethyl-3-{4-[5-hydroxy-2-(4-hydroxy-phenyl)-3-methyl-indol-1-ylmethyl]-phenyl}-acrylamide;
1(E)-N-tert-butyl-3-{4-[5-hydroxy-2-(4-hydroxy-phenyl)-3-methyl-indol-1-ylmethyl]-phenyl}-acrylamide;

(E)-Pyrollidino-3-{4-[5-hydroxy-2-(4-hydroxy-phenyl)-3-methyl-indol-1-ylmethyl]-phenyl}-acrylamide;
(E)-N,N-Dimethyl-3-{4-[5-hydroxy-2-(4-hydroxy-phenyl)-3-methyl-indol-1-ylmethyl]-phenyl}-acrylamide;
(E)-N,N-Dibutyl-3-{4-[5-hydroxy-2-(4-hydroxy-phenyl)-3-methyl-indol-1-ylmethyl]-phenyl}-acrylamide;
(E)-N-Butyl,N'-methyl-3-{4-[5-hydroxy-2-(4-hydroxy-phenyl)-3-methyl-indol-1-ylmethyl]-phenyl}-acrylamide;
(E)-Morpholinino-3-{4-[5-hydroxy-2-(4-hydroxy-phenyl)-3-methyl-indol-1-ylmethyl]-phenyl}-acrylamide;
(E)-3-{4-[5-hydroxy-2-(4-hydroxy-phenyl)-3-methyl-indol-1-ylmethyl]-phenyl}-acrylamide;
(E)-N,Methyl-3-{4-[5-hydroxy-2-(4-hydroxy-phenyl)-3-methyl-indol-1-ylmethyl]-phenyl}-acrylamide;
(E)-N,N-Dibutyl-3-{4-[5-hydroxy-2-(4-fluoro-phenyl)-3-methyl-indol-1-ylmethyl]-phenyl}-acrylamide;
(E)-N-Butyl,N'-Methyl-3-{4-[5-hydroxy-2-(4-fluoro-phenyl)-3-methyl-indol-1-ylmethyl]-phenyl}-acrylamide;

as well as the pharmaceutically acceptable salts and esters thereof.

The compounds of this second subset or subgroup of substituted indole compounds can be produced by the methods described in EP 0 802 184A1, published Oct. 22, 1997, which is incorporated herein by reference, or by other methods known in the art.

A third subset of substituted indole compounds useful with the present invention include those of the formulae VII and VIII:

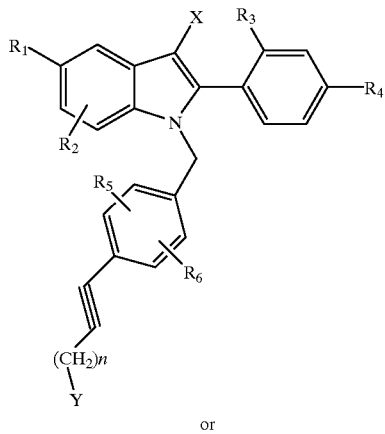

(VII)

or

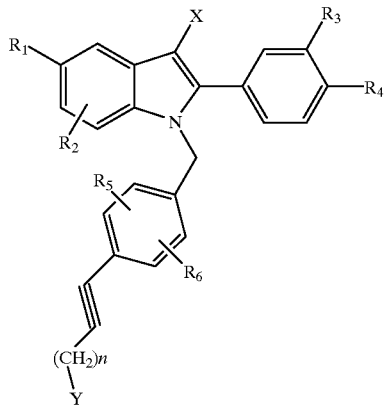

(VIII)

wherein n is 1, 2 or 3 and the variable substituents including $R_1$, $R_2$, $R_3$, $R_4$, $R_5$, $R_6$, n, X, and Y are as defined above, or a pharmaceutically acceptable salt thereof.

Among the preferred compounds of this third subset of substituted indoles are:

2-(4-Hydroxy-phenyl)-3-methyl-1-[4-(3-N, N- dimethyl-1-yl-prop-1-ynyl)-benzyl]-1H-indol-5-ol;
2-(4-Hydroxy-phenyl)-3-methyl-1-[4-(3-piperidin-1-yl-prop-1-ynyl)-benzyl]-1H-indol-5-ol; and
2-(4-Hydroxy-phenyl)-3-methyl-1-[4-(3-pyrrolidin-1-yl-prop-1-ynyl)-benzyl]-1H-indol-5-ol; or pharmaceutically acceptable salts or esters thereof.

The compounds of this third subset or subgroup of substituted indole compounds can be produced by the methods described in U.S. Pat. No. 5,880,137 (Miller et al.), which is incorporated herein by reference, or by other methods known in the art.

Within each of the first, second and third subsets of substituted indole compounds of this invention are further subdivisions of more preferred substituted indole compounds having the general structures I through VIII, above, wherein:

$R_1$ is selected from H, OH or the $C_1$–$C_{12}$ esters or alkyl ethers thereof, halogen;

$R_2$, $R_3$, $R_4$, $R_5$, and $R_6$ are independently selected from H, OH or the $C_1$–$C_{12}$ esters or alkyl ethers thereof, halogen, cyano, $C_1$–$C_6$ alkyl, or trihalomethyl, preferably trifluoromethyl, with the proviso that, when $R_1$ is H, $R_2$ is not OH;

X is selected from H, $C_1$–$C_6$ alkyl, cyano, nitro, trifluoromethyl, halogen;

Y is the moiety

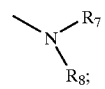

$R_7$ and $R_8$ are selected independently from H, $C_1$–$C_6$ alkyl, or combined by —$(CH_2)_p$—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONH(C_1$–$C_4)$, —$NH_3$, $C_1$–$C_4$ alkylamino, $C_1$–$C_4$ dialkylamino, —$NHSO_2$ ($C_1$–$C_4$), —$NHCO(C_1$–$C_4)$, and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred substituted indole compounds of the present invention are those having the structural formulas I through VIII, above, wherein $R_1$ is OH; $R_2$–$R_6$ are as defined above; X is selected from the group of Cl, $NO_2$, CN, $CF_3$, or $CH_3$; and Y is the moiety

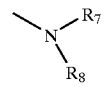

and $R_7$ and $R_8$ are concatenated together as —$(Ch_2)_r$—, wherein r is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONH(C_1$–$C_4)$ alkyl, —NH$_2$, C$_1$–C$_4$ alkylamino, di(C$_1$–C$_4$)alkylamino, —NHSO$_2$(C$_1$–C$_4$)alkyl, —NHCO(C$_1$–C$_4$)alkyl, and —NO$_2$;
and the pharmaceutically acceptable salts thereof.

In another embodiment of the substituted indoles of this invention, when R$_7$ and R$_8$ are concatenated together as —(CH$_2$)$_p$—, wherein p is an integer of from 2 to 6, preferably 4 to 6, the ring so formed is optionally substituted with 1–3 substituents selected from a group containing C$_1$–C$_3$ alkyl, trifluoromethyl, halogen, hydrogen, phenyl, nitro, —CN.

The invention includes sulfate, sulfamates and sulfate esters of phenolic groups in these substituted indoles. Sulfates can be readily prepared by the reaction of the free phenolic compounds with sulfur trioxide complexed with an amine such as pyridine, trimethylamine, triethylamine, etc. Sulfamates can be prepared by treating the free phenolic compound with the desired amino or alkylamino or dialkylamino sulfamyl chloride in the presence of a suitable base such as pyridine. Sulfate esters can be prepared by reaction of the free phenol with the desired alkanesulfonyl chloride in the presence of a suitable base such as pyridine. Additionally, this invention includes compounds containing phosphates at the phenol as well as dialkyl phosphates. Phosphates can be prepared by reaction of the phenol with the appropriate chlorophosphate. The dialkylphosphates can be hydrolyzed to yield the free phosphates. Phosphinates are also claimed where the phenol is reacted with the desired dialkylphosphinic chloride to yield the desired dialkylphosphinate of the phenol.

The invention includes acceptable salt forms of the substituted indoles formed from the addition reaction with either inorganic or organic acids. Inorganic acids such as hydrochloric acid, hydrobromic acid, hydroiodic acid, sulfuric acid, phosphoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and nonprotic) and usually it is preferred to administer a compound of this invention in the form of an acid addition salt. Additionally, this invention includes quaternary ammonium salts of the compounds herein. These can be prepared by reacting the nucleophilic amines of the side chain with a suitably reactive alkylating agent such as an alkyl halide or benzyl halide.

It is understood that the dosage, regimen and mode of administration of these compounds will vary according to the extent of the malady and the individual being treated and will be subject to the judgement of the medical practitioner involved. It is preferred that the administration of one or more of the SSRIs and substituted indole compounds herein begin at a low dose and be increased until the desired effects are achieved.

Effective administration of these compounds may be given at an effective dose of from about 0.1 mg/day to about 500 mg/day. Preferably, administration will be from about 1 mg/day to about 200 mg/day in a single dose or in two or more divided doses. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

When the active ingredient in the formulations and methods of this invention is 1-[4-(2-Azepan-1yl-ethoxy)-benzyl]-2-(4-hydroxy-phenyl)-3-methyl-1H-indol-5-ol, also known as TSE-424, or a pharmaceutically acceptable salt thereof, the preferred daily dosage for oral delivery is from about 0.1 to about 50 mg, preferably from about 2.5 to about 40 mg per day.

When the active ingredient in the formulations and methods of this invention is 2-(4-Hydroxy-phenyl)-3-methyl-1-(4-(2-piperidin-1-yl-ethoxy)-benzyl]-1H-indol-5-ol, also known as ERA-923, or a pharmaceutically acceptable salt form thereof, the preferred daily dosage for oral delivery is from about 0.1 to about 200 mg, preferably from about 2.5 to about 100 mg per day.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

The SSRI compounds of these methods may be administered in regimens and at dosages known in the art. For instance, venlafaxine hydrochloride, which is sold by Wyeth-Ayerst Laboratories under the Effexor® name, has a recommended initial dosage of 75 mg per day, which may be increased to a final daily dosage of up to 225 mg. Average administration is from about 140 to about 180 mg per day. Fluoxetine hydrochloride, marketed by Dista Products Division of Eli Lilly and Company under the Prozac® brandname, may be administered at a daily dosage of from about 20 to about 80 mg. Paroxetine hydrochloride, offered by SmithKline Beecham, Inc. under the Paxil® name, has a recommended daily dosage of from 20 to 50 mg. Sertraline hydrochloride, sold under the Zoloft® name by Pfizer, Inc. may be administered at an initial dose of 25 mg per day and raised to a daily dose of from 50 to 200 mg. Fluvoxamine maleate, sold under the Luvox® tradename by Solvay Pharmaceuticals, Inc., may be given at a starting dose of 50 mg and raised to a daily dosage range of from 100 to 300 mg/day.

The joint administration of the two groups of compounds in these methods will be determined by a medical professional based upon the condition of the recipient and the malady for which the prophylaxis or treatment is provided. Administration of the two compounds may begin simultaneously or one may be introduced into an ongoing regimen of the other.

Preferably, the pharmaceutical compositions of the methods herein are supplied in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The substituted indole compound(s) and the SSRI(s) of the present formulations may be administered in separate dosage units, such as separate pills, tablets, powders, etc., or combined into one formulation. When optimum dosages for the indole compounds and the SSRI of these formulations have been determined, it may preferable to incorporate both into a single formulation for ease of administration. It is also understood that the formulations herein may or may not include other pharmaceutically active components.

This invention also includes kits or packages of pharmaceutical formulations designed for use in the regimens and methods described herein. These kits are preferably designed for daily oral administration over the specified term or cycle of administration, preferably for the number of prescribed oral administrations per day, and organized so as to indicate a single oral formulation or combination of oral formulations to be taken on each day of the regimen or cycle. Preferably each kit will include oral tablets to be taken on each the days specified, in some embodiments one oral tablet will contain each of the combined daily dosages indicated and in other embodiments the administrations of the separate compounds will be present in separate formulations or compositions. It is most preferable that the package or kit shall have a calendar or days-of-the-week designation directing the administration of the appropriate compositions on the appropriate day or time.

A preferred combination of this invention includes pharmaceutical compositions of 1-[4-(2-Azepan-1yl-ethoxy)-benzyl]-2-(4-hydroxy-phenyl)-3-methyl-1H-indol-5-ol, or a pharmaceutically acceptable salt thereof, packaged and/or utilized in combination with venlafaxine, or a pharmaceutically acceptable salt thereof. Another comprises 2-(4-Hydroxy-phenyl)-3-methyl-1-(4-(2-piperidin-1-yl-ethoxy)-benzyl]-1H-indol-5-ol, or pharmaceutically acceptable salt thereof, packaged and/or used in combination with venlafaxine, or a pharmaceutically acceptable salt thereof.

Solid oral formulations, preferably in the form of a film coated tablet or capsule, useful for this invention include the active substituted indole pharmacological agents disclosed herein in combination with carrier or excipient systems having the components:

a) a filler and disintegrant component comprising from about 5% to about 82% by weight (wght) of the total formulation, preferably between about 30% and about 80% of the formulation, of which from about 4% to about 40% by weight of the total formulation comprises one or more pharmaceutically acceptable disintegrants;

b) optionally, a wetting agent comprising from about 0.2 to about 5% of the composition (wght), such as selected from the group of sodium lauryl sulfate, polyoxyethylene sorbitan fatty acid esters, polyoxyethylene alkyl ethers, sorbitan fatty acid esters, polyethylene glycols, polyoxyethylene castor oil derivatives, docusate sodium, quaternary ammonium compounds, sugar esters of fatty acids and glycerides of fatty acids;

c) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parrafins, hydrogenated vegetable oils, leucine, polyethylene glycols, metallic lauryl sulfates and sodium chloride; and d) optionally, a glidant comprising from about 0.1% to about 10% (wght) of the composition, the glidant selected from those known in the art, including from the group of silicon dioxide, talc, metallic stearates, calcium silicate, or metallic lauryl sulfates.

While the formulations described herein may be used in an uncoated or non-encapsulated solid form, preferably the final compositions are coated or encapsulated. The pharmacological compositions may be optionally coated with a film coating, preferably comprising from about 0.3% to about 8% by weight of the overall composition. Film coatings useful with the present formulations are known in the art and generally consist of a polymer (usually a cellulosic type of polymer), a colorant and a plasticizer. Additional ingredients such as wetting agents, sugars, flavors, oils and lubricants may be included in film coating formulations to impart certain characteristics to the film coat. The compositions and formulations herein may also be combined and processed as a solid, then placed in a capsule form, such as a gelatin capsule.

The filler component listed above may utilize the filler or binder components known in the art for solid oral formulations. Pharmaceutically acceptable fillers or binding agents selected from those known in the art including, but not limited to, lactose, microcrystalline cellulose, sucrose, mannitol, calcium phosphate, calcium carbonate, powdered cellulose, maltodextrin, sorbitol, starch, or xylitol.

In conjunction with or in place of the materials listed above for the filler component, the present formulations utilize disintegrant agents. These disintegrants may be selected from those known in the art, including pregelatinized starch and sodium starch glycolate. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.). The disintegrant(s) useful herein will comprise from about 4% to about 40% of the composition by weight, preferably from about 15% to about 35%, more preferably from about 20% to about 35%. Some components may have multiple functions in the formulations of this invention, acting e.g. as both a filler and a disintegrant, such a component may be referred to as a filler disintegrant and its function in a specific formulation may be singular even though its properties may allow multiple functionality.

The pharmaceutical formulations and carrier or excipient systems herein preferably also contain an antioxidant or a mixture of antioxidants, most preferably ascorbic acid. Other antioxidants which may be used include sodium ascorbate and ascorbyl palmitate, preferably in conjunction with an amount of ascorbic acid. A preferable range for the antioxidant(s) is from about 0.5% to about 15% by weight, most preferably from about 0.5% to about 5% by weight.

Among the formulations of this invention are pharmaceutical formulations containing a pharmaceutically effective amount of an active pharmacological agent and a carrier or excipient system comprising:

a) a filler and disintegrant component comprising between about 50% and about 87% of the formulation, with from about 4% to about 40% of the formulation comprising one or more disintegrant agents;

b) a wetting agent comprising between about 0.5% and about 2.7% of the formulation;

c) a lubricant comprising between about 0.2% and about 5.5% of the formulation; and d) a glidant comprising between about 0.1% and about 5.5% of the formulation.

The percentages listed in the formulations above indicate percentages by weight of the total weight of the components listed from a) to d). The formulations above also preferably contain an optional antioxidant component, preferably ascorbic acid, at a concentration of from about 0.5% to about 5.5% by weight of the formulation. The formulations are also preferably contained within a pharmaceutically acceptable capsule, such as a gel capsule, or coated with a film coating comprising from about 0.3% to about 8% by weight of the formulation.

This invention also comprises a pharmaceutical carrier or excipient systems useful in pharmaceutical compositions utilizing as an active ingredient one or more of the compounds described herein, or a pharmaceutically acceptable salt thereof, as described herein. These pharmaceutical carrier or excipient systems comprise, by weight:

a) a filler and disintegrant component comprising between about 54% and about 80% of the formulation, with the disintegrant agent(s) therein comprising from about 4% to about 40% by weight of the overall formulation;

b) a wetting agent comprising between about 0.55% and about 2.5% of the formulation;

c) a lubricant comprising between about 0.2% and about 5.5% of the formulation; and d) a glidant comprising between about 0.1% and about 5.0% of the formulation.

The more preferred carrier or excipient systems above also optionally and preferably contain an antioxidant component, preferably ascorbic acid, at a concentration of from about 0.1% to about 5.0% by weight.

Among the carrier or excipient systems of this invention are those comprising:

a) a filler and disintegrant component, as described above, comprising between about 50% and about 87% of the formulation, the disintegrant(s) therein comprising from about 25% to about 35% of the formulation, by weight;

b) a wetting agent comprising between about 0.55% and about 2.7% of the formulation;

c) a lubricant comprising between about 0.2% and about 5.5% of the formulation;

d) a glidant comprising between about 0.1% and about 5.5% of the formulation; and e) an antioxidant component, preferably ascorbic acid, at a concentration of from about 0.1% to about 5.5% by weight.

EXAMPLE 1

TSE-424 Acetate—Rapid Dissolution Formulations

| Ingredient | without Ascorbic Acid | with Ascorbic Acid |
| --- | --- | --- |
| TSE-424 acetate, micronized* | 10.00 | 10.00 |
| Lactose NF fast flow | 33.10 | 31.60 |
| Microcrystalline Cellulose, NF (Avicel PH101) | 25.00 | 25.00 |
| Starch 1500 | 20.00 | 20.00 |
| Sodium Lauryl Sulfate NF | 1.50 | 1.50 |
| Sodium Starch Glycolate | 10.00 | 10.00 |
| Ascorbic Acid USP | — | 1.5 |
| Syloid 244 FP | 0.15 | 0.15 |
| Magnesium Stearate | 0.25 | 0.25 |

*Amount in formula is adjusted for actual potency of TSE-424 as free base. Corresponding adjustment made with Lactose.

The formulations given above in Table 1 were prepared by incorporating a portion of the excipients in the granulation and a portion is also added in the final blending steps as dry powders. A dissolution profile generated for the formulations demonstrated almost 90% release of the drug in 30 minutes. Thus, the unique combination of disintegrants and soluble diluents plus the incorporation of both granulated and powdered solids into the composition ensures the fastest release of drug.

Wet granulation of the formulations as described in Table 1 may be carried out by mixing the drug and ascorbic acid with a portion of the lactose, microcrystalline cellulose, pregelatinized starch and sodium starch glycolate. The sodium lauryl sulfate is dissolved in the water and used to granulate the mixture of powders in a high shear mixer. The granulation is dried in a fluid bed dryer to a moisture of 2–3%. The particle size of the dried granulation is controlled by passing through a mill equipped with knife-edged blades and using a 20- or 30-mesh screen. The silicon dioxide and remaining lactose, microcrystalline cellulose, pregelatinized starch, and sodium starch glycolate are mixed with the milled granulation in a tumble-type mixer. The final blend is prepared by adding magnesium stearate to the tumble-type mixer and mixing. Compression is carried out on a rotary tablet press using appropriate size tooling. Coating is performed in conventional coating pans and applying the coating suspension to achieve a suitable film coat.

EXAMPLE 2

Modified TSE-424 Formulation

| Ingredient | % w/w 5% granulation |
| --- | --- |
| TSE-424 acetate, micronized[a] | 5.00 |
| Lactose NF | 41.00 |
| Microcrystalline Cellulose, NF | 35.00 |
| Pregelatinized Starch NF | 10.00 |
| Sodium Lauryl Sulfate NF | 1.50 |

-continued

| Ingredient | % w/w 5% granulation |
|---|---|
| l-Ascorbic Acid USP | 1.50 |
| Sodium Starch Glycolate NF | 5.50 |
| Magnesium Stearate NF | 0.50 |
| Pur. Water USP[b] | qs |

[a]Amount in formula is adjusted for actual potency of TSE-424 as free base. Corresponding adjustment made with Lactose.
[b]Used in process but does not appear in the final product.

EXAMPLE 3

ERA-923 Formulations

| Ingredient | 10.86% granulation | 11.19% granulation | 17.5% granulation | 17.9% granulation |
|---|---|---|---|---|
| ERA-923, micronized[a] | 10.867 | 11.193 | 17.489 | 17.909 |
| Lactose NF | 29.000 | 29.000 | 17.380 | 18.000 |
| Microcrystalline Cellulose, NF | 40.633 | 42.807 | 38.000 | 39.090 |
| Pregelatinized Starch NF | 10.000 | 10.000 | 14.630 | 15.000 |
| Sodium Lauryl Sulfate NF | 2.500 | — | 2.500 | — |
| l-Ascorbic Acid USP | 1.500 | 1.500 | 1.500 | 1.500 |
| Sodium Starch Glycolate NF | 5.000 | 5.000 | 8.000 | 8.000 |
| Magnesium Stearate NF | 0.500 | 0.500 | 0.500 | 0.500 |
| Pur. Water USP[b] | qs | qs | qs | qs |

[a]As the Hydrochloride Monohydrate. Quantity is adjusted based on the actual potency (theory = 89.34%).
[b]Used in process but does not appear in the final product. ERA-923 tablets are compressed to a tablet weight of up to 640 mg to achieve the target dose (up to 100 mg). Tablets may then be film coated.

EXAMPLE 4

TSE424 at 5% Granulation

A preferred carrier or excipient system for formulating a granulation of from about 2 to about 8% by weight of one of the active pharmacological agents of this invention, preferably about 5%, may be produced utilizing the carrier or excipient components on a weight percentage; lactose from about 32% to about 38%, microcrystalline cellulose from about 32% to about 38%, pregelatinized starch from about 12% to about 16%, ascorbic acid from about 1% to about 2%, sodium lauryl sulfate from about 1% to about 2%, sodium starch glycolate from about 4% to about 8%, silicon dioxide from about 0.1% to about 0.2% and magnesium stearate from about 0.3% to about 0.7%.

A formulation of this invention utilizing TSE-424 as the active ingredient at a 5% granulation was prepared utilizing the components listed below in a granulation part of components and a dry part.

| Item No. | Ingredients | Mg/Unit |
|---|---|---|
| Granulation Part: | | |
| 1 | TSE-424 acetate | 5.00 |
| 2 | Lactose NF | 26.60 |
| 3 | Microcrystalline Cellulose NF | 25.00 |
| 4 | Pregelatinized Starch NF | 10.00 |
| 5 | Ascorbic Acid USP | 1.50 |
| 6 | Sodium Lauryl Sulfate NF | 1.50 |
| 7 | Sodium Starch Glycolate NF | 4.00 |
| 8 | Water, Purified USP | Q.S. |
| | | 73.60 |
| Dry Part: | | |
| 9 | Lactose NF (fast flo) | 9.75 |
| 10 | Microcrystalline Cellulose NF | 10.00 |
| 11 | Pregelatinized Starch NF | 4.00 |
| 12 | Sodium Starch Glycolate NF | 2.00 |
| 13 | Silicon Dioxide NF | 0.15 |
| 14 | Magnesium Stearate NF | 0.50 |
| | | 100.00 |

A film coat of White Opadry I (YS-1-18027-A) was applied to the tablets, which were compressed as follows:

| Dose of TSE-424 | tablet weight, mg | mg of film coat applied/tablet |
|---|---|---|
| 5 mg | 100 | 6.0 |
| 10 mg | 200 | 8.0 |
| 20 mg | 400 | 13.0 |

What is claimed:

1. A method for treatment of depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome in a mammal, the method comprising administering to a mammal in need thereof a pharmaceutically effective amount of a selective serotonin reuptake inhibitor, or a pharmaceutically acceptable salt thereof, and a pharmaceutically effective amount of a compound of the formulae I or II:

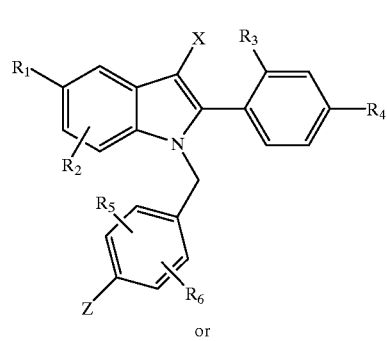

or

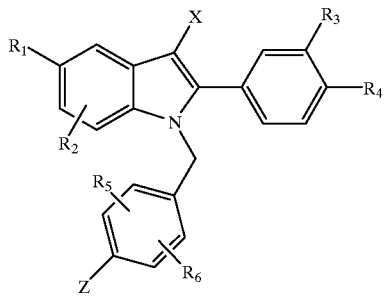

wherein Z is a moiety selected from the group of:

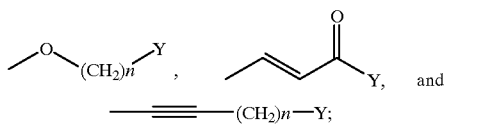

wherein:
  $R_1$ is selected from H, OH or the $C_1-C_{12}$ esters or $C_1-C_{12}$ alkyl ethers thereof, benzyloxy, halogen, $C_1-C_4$ halogenated ethers, trifluoromethyl ether and trichloromethyl ether,
  $R_2$, $R_3$, $R_5$ and $R_6$ are independently selected from H, OH or the $C_1-C_{12}$ esters or $C_1-C_{12}$ alkyl ethers thereof, halogens, $C_1-C_4$ halogenated ethers, cyano, $C_1-C_6$ alkyl, and trifluoromethyl, with the proviso that, when $R_1$ is H, $R_2$ is not OH;
  $R_4$ is selected from H, OH or the $C_1-C_{12}$ esters or $C_1-C_{12}$ alkyl ethers thereof, halogens, $C_1-C_4$ halogenated ethers, benzyloxy, cyano, $C_1-C_6$ alkyl, and trifluoromethyl;
  X is selected from H, $C_1-C_6$ alkyl, cyano, nitro, trifluoromethyl, and halogen;
  n is 1, 2 or 3;
  Y is selected from:
    a) the moiety:

wherein $R_7$ and $R_8$ are independently selected from the group of H, $C_1-C_6$ alkyl, and phenyl optionally substituted by CN, $C_1-C_6$ alkyl, $C_1-C_6$ alkoxy, halogen, —OH, —$CF_3$, or —$OCF_3$;
    b) a five-membered saturated, unsaturated or partially unsaturated heterocycle containing up to two heteroatoms selected from the group consisting of —O—, —NH—, —N($C_1$ $C_4$ alkyl)-, —N═, and —S(O)$_m$—, wherein m is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —$CO_2H$—, —CN—, —$CONHR_1$—, —$NH_2$—, $C_1-C_4$ alkylamino, di($C_1-C_4$)alkylamino, —$NHSO_2R_1$—, —$NHCOR_1$—, —$NO_2$, and phenyl optionally substituted with 1–3 ($C_1-C_4$)alkyl;
    c) a six-membered saturated, unsaturated or partially unsaturated heterocycle containing up to two heteroatoms selected from the group consisting of —O—, —NH—, —N($C_1$ $C_4$ alkyl)-, —N═, and —S(O)$_m$—, wherein m is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —$CO_2H$—, —CN—, —$CONHR_1$—, —$NH_2$—, $C_1-C_4$ alkylamino, di($C_1-C_4$)alkylamino, —$NHSO_2$—, —$NHCOR_1$—, —$NO_2$, and phenyl optionally substituted with 1–3 ($C_1-C_4$)alkyl;
    d) a seven-membered saturated, unsaturated or partially unsaturated heterocycle containing up to two heteroatoms selected from the group consisting of —O—, —NH—, —N($C_1C_4$ alkyl)-, —N═, and —S(O)$_m$—, wherein m is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —$CO_2H$—, —CN—, —$CONHR_1$—, —$NH_2$—, $C_1-C_4$ alkylamino, di($C_1-C_4$)alkylamino, —$NHSO_2R_1$—, —$NHCOR_1$—, —$NO_2$, and phenyl optionally substituted with 1–3 ($C_1-C_4$)alkyl; or
    e) a bicyclic heterocycle containing from 6–12 carbon atoms either bridged or fused and containing up to two heteroatoms selected from the group consisting of —O—, —NH—, —N($C_1C_4$ alkyl)-, and —S(O)$_m$—, wherein m is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —$CO_2H$—, —CN—, —$CONHR_1$—, —$NH_2$—, $C_1-C_4$ alkylamino, di($C_1-C_4$)alkylamino, —$NHSO_2R_1$—, —$NHCOR_1$—, —$NO_2$, and phenyl optionally substituted with 1–3 ($C_1-C_4$) alkyl;

or a pharmaceutically acceptable salt thereof.

2. The method of claim 1 wherein in the compound of the formulae I or II:
  $R_1$ is selected from H, OH or the $C_1-C_{12}$ esters or alkyl ethers thereof, benzyloxy, and halogen;
  $R_2$, $R_3$, $R_5$, and $R_6$ are independently selected from H, OH or the $C_1-C_{12}$ esters or alkyl ethers thereof, halogen, cyano, $C_1-C_6$ alkyl, and trihalomethyl; with the proviso that, when $R_1$ is H, $R_2$ is not OH;
  $R_4$ is selected from H, OH or the $C_1-C_{12}$ esters or alkyl ethers thereof, benzyloxy, halogen, cyano, $C_1-C_6$ alkyl, and trihalomethyl;
  X is selected from H, $C_1-C_6$ alkyl, cyano, nitro, trifluoromethyl, and halogen;

Y is the moiety:

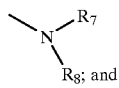

R$_7$ and R$_8$ are selected independently from H, and C$_1$–C$_6$ alkyl, or combined by —(CH$_2$)$_p$—, wherein p is an integer of from 2 to 6, so as to form a ring, the ring being optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_3$, C$_1$–C$_4$ alkylamino, C$_1$–C$_4$ dialkylamino, —NHSO$_2$(C$_1$–C$_4$), —NHCO(C$_1$–C$_4$), and —NO$_3$;
or a pharmaceutically acceptable salt thereof.

3. The method of claim 2 wherein, in the compound of the formulae I or II, the ring formed by a the combination of R$_7$ and R$_8$ by —(CH$_2$)$_p$— is selected from aziridine, azetidine, pyrrolidine, piperidine, hexamethyleneamine and heptamethyleneamine.

4. The method of claim 1 utilizing a compound of the formulae I or II, wherein R$_1$ is OH; R$_2$–R$_6$ are as defined in claim 1; X is selected from the group of Cl, NO$_2$, CN, CF$_3$, and CH$_3$; and Y is the moiety:

and R$_7$ and R$_8$ are concatenated together as —(CH$_2$)$_r$—, wherein r is an integer of from 4 to 6, to form a ring optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$) alkyl, —NH$_2$, C$_1$–C$_4$ alkylamino, di(C$_1$–C$_4$)alkylamino, —NHSO$_2$ (C$_1$–C$_4$)alkyl, —NHCO(C$_1$–C$_4$)alkyl, and —NO$_2$;
or a pharmaceutically acceptable salt thereof.

5. The method of claim 1 wherein the SSRI is selected from the group of venlafaxine, fluoxetine, paroxetine, sertraline, and fluvoxamine, or a pharmaceutically acceptable salt thereof.

6. The method of claim 1 wherein the disorder is depression.

7. The method of claim 1 wherein the disorder is pain.

8. The method of claim 1 wherein the disorder is generalized anxiety disorder.

9. The method of claim 1 wherein the disorder is anxiety.

10. A method for treating depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nermosa, or Shy Drager Syndrome in a mammal, the method comprising administering to a mammal in need thereof a pharmaceutically effective amount of a SSRI, or a pharmaceutically acceptable salt thereof, and a pharmaceutically effective amount of a compound of the formulae I or II:

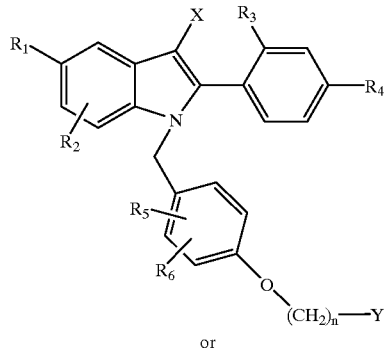

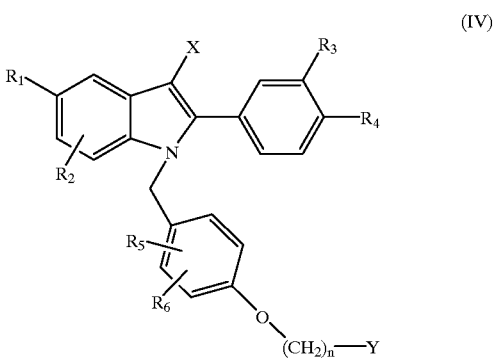

wherein R$_1$, R$_2$, R$_3$, R$_4$, R$_5$, R$_6$, n, X, and Y are as defined in claim 1, or a pharmaceutically acceptable salt thereof.

11. A method for treating depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome in a mammal, the method comprising administering to a mammal in need thereof a pharmaceutically effective amount of a SSRI, or a pharmaceutically acceptable salt thereof, and a pharmaceutically effective amount of a compound of the formulae (V) or (VI):

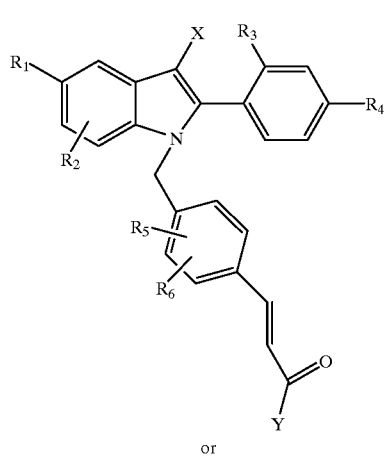

or (VI)

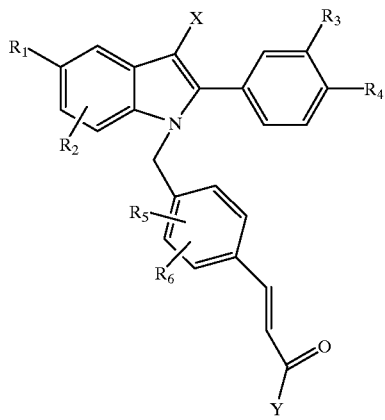

wherein $R_1$, $R_2$, $R_3$, $R_4$, $R_5$, $R_6$, X, and Y are as defined in claim 1, or a pharmaceutically acceptable salt thereof.

12. A method for treating depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome in a mammal, the method comprising administering to a mammal in need thereof a pharmaceutically effective amount of a SSRI, or a pharmaceutically acceptable salt thereof, and a pharmaceutically effective amount of a compound of the formulae VII and VIII:

(VII)

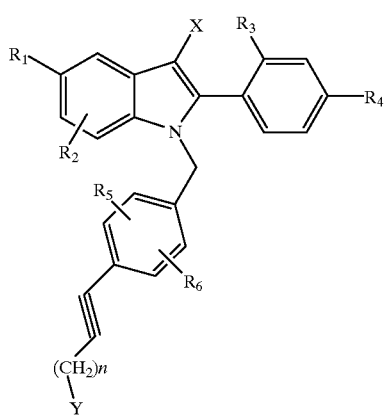

or (VIII)

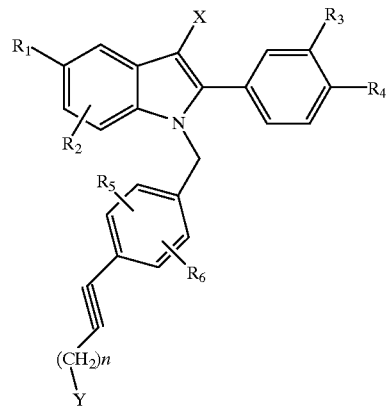

wherein $R_1$, $R_2$, $R_3$, $R_4$, $R_5$, $R_6$, n, X, and Y are as defined in claim 1, or a pharmaceutically acceptable salt thereof.

13. A method for treating depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome in a mammal, the method comprising administering to a mammal in need thereof a pharmaceutically effective amount of 1-[4-(2-Azepan-1-yl-ethoxy)-benzyl]-2-(4-hydroxy-phenyl)-3-methyl-1H-indol-5-ol, and a pharmaceutically effective amount of a SSRI, or a pharmaceutically acceptable salt thereof.

14. The method of claim 13 wherein the SSRI is selected from the group of venlafaxine, fluoxetine, paroxetine, sertraline, and fluvoxamine, or a pharmaceutically acceptable salt thereof.

15. A method for treating depression, anxiety, generalized anxiety disorder (GAD), hot flush, post partum depression, premenstrual syndrome, obesity, obsessive compulsive disorder, post-traumatic stress disorder, social phobia, disruptive behavior disorders, impulse control disorders, borderline personality disorder, chronic fatigue disorder, premature ejaculation, pain, attention deficit disorders, with and without hyperactivity, Gilles de la Tourette syndrome, bulimia nervosa, or Shy Drager Syndrome in a mammal, the method comprising administering to a mammal in need thereof a pharmaceutically effective amount of 2-(Hydroxy-phenyl)-3-methyl-1-[4-(2-piperidin-1-yl-ethoxy)-benzyl]-1H-indol-5-ol and a pharmaceutically effective amount of a SSRI, or a pharmaceutically acceptable salt thereof.

16. The method of claim 15 wherein the SSRI is selected from the group of venlafaxine, fluoxetine, paroxetine, sertraline, fluvoxamine, or a pharmaceutically acceptable salt thereof.

* * * * *